(12) United States Patent
Welch et al.

(10) Patent No.: US 11,129,629 B2
(45) Date of Patent: Sep. 28, 2021

(54) THROMBUS EXTRACTION CATHETER

(71) Applicant: NorMedix, Inc., Eden Prairie, MN (US)

(72) Inventors: Jeffrey M. Welch, Maple Grove, MN (US); Karl V. Ganske, Hopkins, MN (US); Gregg Stuart Sutton, Maple Grove, MN (US)

(73) Assignee: NorMedix, Inc., Eden Prairie, MN (US)

( * ) Notice: Subject to any disclaimer, the term of this patent is extended or adjusted under 35 U.S.C. 154(b) by 125 days.

(21) Appl. No.: 16/166,783

(22) Filed: Oct. 22, 2018

(65) Prior Publication Data

US 2019/0117240 A1   Apr. 25, 2019

Related U.S. Application Data

(63) Continuation of application No. 14/786,851, filed as application No. PCT/US2014/035142 on Apr. 23, 2014, now Pat. No. 10,130,379.

(Continued)

(51) Int. Cl.
*A61B 17/22* (2006.01)
*A61L 29/04* (2006.01)
(Continued)

(52) U.S. Cl.
CPC ............... *A61B 17/22* (2013.01); *A61L 29/02* (2013.01); *A61L 29/041* (2013.01); *A61L 29/06* (2013.01); *A61L 29/085* (2013.01); *A61L 29/106* (2013.01); *A61L 29/18* (2013.01); *A61M 25/005* (2013.01); *A61B 2017/22039* (2013.01); *A61B 2017/22042* (2013.01); *A61B 2017/22079* (2013.01); *A61B 2090/3966* (2016.02);
(Continued)

(58) Field of Classification Search
CPC ......... A61B 17/22; A61B 2017/22079; A61M 25/0043; A61M 25/005; A61M 25/0052; A61M 25/0067; A61M 25/0068; A61M 25/0069; A61M 2025/0177
See application file for complete search history.

(56) References Cited

U.S. PATENT DOCUMENTS 5,549,556 A  *  8/1996  Ndondo-Lay ....... A61M 25/104
                                                      604/103.1
6,036,670 A  *  3/2000  Wijeratne ........... A61M 25/005
                                                      604/526

(Continued)

FOREIGN PATENT DOCUMENTS

EP     1639951 A1    3/2006
EP     2988684       3/2016

(Continued)

OTHER PUBLICATIONS

"U.S. Appl. No. 14/786,851, Non Final Office Action dated Dec. 14, 2017", 5 pgs.

(Continued)

*Primary Examiner* — Thomas McEvoy
(74) *Attorney, Agent, or Firm* — Schwegman Lundberg & Woessner, P.A.

(57) ABSTRACT

Embodiments of the invention include a multi-lumen catheter for extracting or aspirating a blood clot or thrombus from arterial or veinous sites. Other embodiments are also included herein.

17 Claims, 1 Drawing Sheet

Related U.S. Application Data

(60) Provisional application No. 61/815,160, filed on Apr. 23, 2013.

(51) Int. Cl.

| | | |
|---|---|---|
| *A61L 29/06* | (2006.01) | |
| *A61M 25/00* | (2006.01) | |
| *A61L 29/02* | (2006.01) | |
| *A61L 29/08* | (2006.01) | |
| *A61L 29/10* | (2006.01) | |
| *A61L 29/18* | (2006.01) | |
| *A61M 25/01* | (2006.01) | |
| *A61B 90/00* | (2016.01) | |

(52) U.S. Cl.
CPC ............... *A61M 2025/0046* (2013.01); *A61M 2025/0059* (2013.01); *A61M 2025/0183* (2013.01)

(56) References Cited

U.S. PATENT DOCUMENTS

| | | |
|---|---|---|
| 6,152,909 A | 11/2000 | Bagaoisan et al. |
| 7,608,063 B2 | 10/2009 | Le et al. |
| 10,130,379 B2 | 11/2018 | Welch et al. |
| 2006/0276774 A1 | 12/2006 | Mori |
| 2007/0106211 A1 | 5/2007 | Provost-tine et al. |
| 2009/0270800 A1 | 10/2009 | Spurchise et al. |
| 2012/0016344 A1 | 1/2012 | Kusakabe |
| 2013/0090632 A1* | 4/2013 | Tahara .............. A61M 25/0009 604/526 |
| 2016/0106446 A1 | 4/2016 | Welch et al. |

FOREIGN PATENT DOCUMENTS

| | | |
|---|---|---|
| JP | 2010057831 A | 3/2010 |
| WO | WO-2014176332 | 10/2014 |

OTHER PUBLICATIONS

"U.S. Appl. No. 14/786,851, Notice of Allowance dated Jul. 13, 2018", 10 pgs.
"U.S. Appl. No. 14/786,851, Response filed Apr. 16, 2018 to Non Final Office Action dated Dec. 14, 2017", 8 pgs.
"European Application Serial No. 14789021.4, Communication pursuant to Rules 161(2) and 162 EPC dated Dec. 11, 2015", 2 pgs.
"European Application Serial No. 14789021.4, Extended European Search Report dated Nov. 23, 2016", 8 pgs.
"European Application Serial No. 14789021.4, Response filed Oct. 4, 2017 to Extended European Search Report dated Nov. 23, 2016", 9 pgs.
"European Application Serial No. 14789021.4, Communication Pursuant to Article 94(3) EPC dated Mar. 23, 2020", 4 pgs.
"European Application Serial No. 14789021.4, Response filed Jul. 30, 2020 to Communication Pursuant to Article 94(3) EPC dated Mar. 23, 2020", 18 pgs.

\* cited by examiner

THROMBUS EXTRACTION CATHETER

CLAIM OF PRIORITY

This application is a continuation of U.S. patent application Ser. No. 14/786,851, filed on Apr. 14, 2016, which is a U.S. National Stage Filing under 35 U.S.C. § 371 of International Patent Application Serial No. PCT/US/2014/035142, filed Apr. 23, 2014, and published on Oct. 30, 2014 as WO 2014/176332, which claims priority to U.S. Provisional Patent Application No. 61/815,160, filed Apr. 23, 2013, the contents of which are herein incorporated by reference in their entirety.

FIELD OF THE INVENTION

The present invention relates to multi-lumen catheter for extracting or aspirating blood clot or thrombus from arterial or veinous sites.

BACKGROUND

In coronary and peripheral interventions requiring revascularization, many times a clot has formed proximal to the atherosclerotic lesion. Extraction of the clot prior to angioplasty or stenting can be preferred to reduce the possibility of distal emboli.

Systems available to physicians, including distal protection filters and mechanical clot maceration devices, are subject to limitations including difficult placement and manipulation, time to prepare and deliver devices, required occlusion of blood flow, and other complications such as arterial spasm and dissection. These devices in general are over-complicated and bring additional risks to the procedure. In addition, problems associated with the currently available thrombus extraction catheters include; kinking, buckling, stretching and ovaling. These problems all reduce the ability to quickly extract thrombus or navigate to the treatment site. The device of this invention solves these limitations by providing a means to quickly and directly remove the thrombus burden present in arterial and veinous interventions while maintaining the device mechanical integrity.

SUMMARY OF THE INVENTION

Embodiments of the invention include a two lumen catheter for use in arterial or veinous interventional procedures for extracting thrombus or a clot. The catheter can comprise a first main lumen for sucking or aspirating the blood clot. The first main lumen extends from the distal tip to the proximal end. The distal portion of the first main lumen can comprise metal and can be constructed from a swaged, tightly spaced metal coil, such that the individual coil wire cross-section are substantially rectangular in shape. A proximal portion of the first lumen can comprise metal tubing and be attached to the distal portion. The proximal portion can terminate at its proximal end with a luer adapter.

A second guidewire passing lumen extending from the distal tip and exiting or terminating at a point proximal of the distal tip at a distance of 1 cm to 50 cm. The guidewire lumen can be attached adjacent to the outside wall of the first, main lumen.

A distal tip structure attached to the distal portion of the first main lumen is angled at its distal end 30-60 degrees from the central axis of the lumen. The distal tip can be attached by metal fusion to the distal coil portion. The distal tip can be externally coated with gold plating for enhanced radiopactiy.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

DETAILED DESCRIPTION OF THE INVENTION

Figure 1:
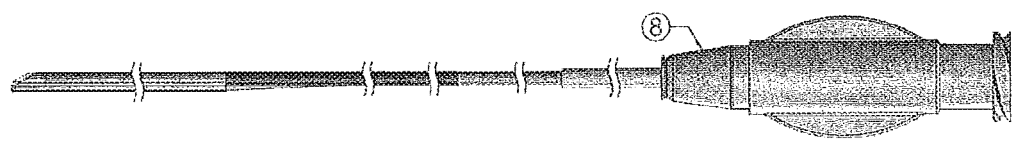
FIG. 1 is a perspective view of the device.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The catheter device of this invention is a two-lumen catheter that is manipulated or navigated to the arterial or veinous site where thrombus is present. One of the lumens in the catheter of this invention is for railing over a guidewire (for example an 0.014") that is typically used to access the arterial or veinous site or branch. The catheter can be railed over a guidewire and inserted within an interventional guide catheter. The second lumen of the catheter is used mainly for sucking or aspirating the thrombus/clot. This is accomplished by attaching a large capacity syringe to the proximal second lumen luer adapter and pulling a vacuum on the syringe so as to cause suction at the distal tip of the catheter. In one embodiment, the distal tip of the catheter of this invention has a guard strut protecting the distal tip opening from being sucked against the arterial or veinous wall. In another embodiment, the distal tip is slightly angled to provide maximum cross-sectional opening at the tip.

The device of this invention can solve the problems associated with current guide catheter technology by providing a thrombus catheter design, construction and materials. The thrombus catheter design of this invention can comprise a composite built tube that is fabricated using a specially wound metal inner layer and jacketed with very thin layers of polymer inside and out. The metallic inner layer can be made using a multi-filar, such as 6-20 filars, helically wound wire structure. In an embodiment, the multi-filar helically wound wire structure can include stainless steel. In an embodiment of this invention, the helical structure can be swaged such that each individual wire strand in partially rectangular in cross-section and can result in a tightly spaced, close fitting, or intimate wire matrix. In an embodiment, the catheter can be made using a non-swaged, round, circular, oval, elliptical, square or rectangular wire. In an embodiment, the multi-filar structure wires can be coated with PTFE, such as prior to forming the multi-filar configuration. In an embodiment, the typical wall thickness of the inner metal structure can be at least 1.5 thousandths of an inch think and no more than 10 thousandths of an inch thick. In an embodiment, the multi-filar layer can have welded terminations.

The helically wound metal structure can provide a significant improvement in mechanical integrity of the catheter tube compared to current catheters with respect to kinking, buckling, flexibility, radial strength, and maintaining circularity of the catheter lumen cross-section. This marked improvement can be achieved by the significant increase in the amount of metal in the catheter. For instance, current interventional catheters that are composite built or wire braid reinforced have total cross-sectional metallic component in the range of 5-10%. The catheter can have a total cross-sectional metallic component of 35-65%. The transmission of mechanical energy through this significantly higher modulus composite can result in significantly higher performance.

The thrombus extraction catheter can also comprise outer and inner polymer 25 layers or jacket made of various polymers, such as nylon, PTFE, Pebax®, Polyurethane, a hydrophilic polymer, or other similar polymers. The inner polymer layer can be disposed on the inside surface of the catheter, such as the surface defining a lumen. The outer polymer layer can be disposed on the outside surface of the catheter, such as the surface that is external to a lumen. In an embodiment, the outer or inner 30 polymer layers can include a composite of two or more polymers, such as a composite of PTFE and Pebax®. In an embodiment, the outer and inner polymer layers can include different materials, such as the inner layer including PTFE and the outer layer including Pebax®. In an embodiment, the outer or inner polymer layer can include two or more layers, such as the outer polymer layer including two layer of Pebax®. The polymer layers can be attached to the metal structure, such as by thermal polymer heat-shrinking or reflow. The polymer layers can be heat shrinkable, such as to allow it to be formed tightly only the helical multi-filar structure. The resultant wall thickness of the polymer layers can be between 1.0-3.0 thousandths of an inch for each layer.

The construction and performance of the thrombus extraction catheter makes it ideally suited for interventional cases where significant vascular tortuosity is encountered such as using a radial artery access or using a femoral approach on an obese patient.

The guide catheter can also comprise an angled, soft (low durometer) polymer distal tip, a radiopaque distal marker band, and a proximal luer adapter. The thrombus extraction catheter of this invention could be made for instance in sizes from 3F-8F and in lengths of 80-175 cm.

In reference to the Figures, FIG. 1 shows a perspective view of a catheter. The catheter can include a luer adapter 8. In an embodiment, the luer adapter 8 can be coupled or attached to the proximal end of the catheter. The luer adapter 8 can be configured to couple or attach a suction device to the catheter. The outer diameter of the catheter, such as the outer diameter of the main tubular shaft can be 0.039-0.105 inches.

Figure 2:
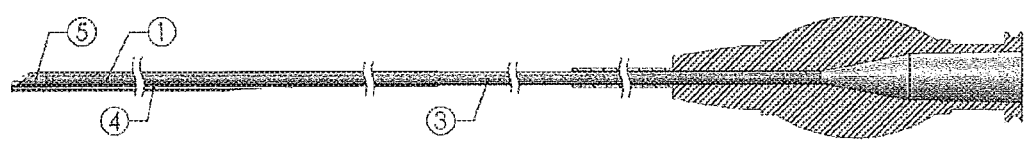
FIG. 2 is a section view of the device showing its parts

FIG. 2 shows a cross-section of the catheter. The catheter can include a first main lumen 1, a second lumen 4, a distal tip structure 5, and a proximal portion 3. The second lumen 4 can be configured for a guidewire to pass through the lumen. The distal tip structure 5 can be coupled to the distal portion of the first main lumen, such as with metal fusion. The distal tip structure 5 can be angled at its distal end, such as from 30-60 degrees from the central axis of the lumen.

Figure 3:
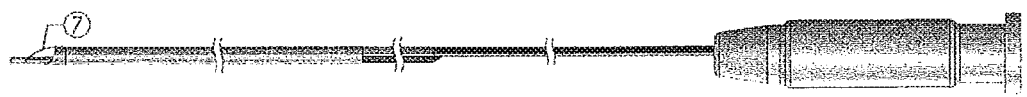
FIG. 3 is a perspective view of the device with further distal tip embodiment

FIG. 3 shows a perspective view of a catheter with an alternative embodiment of the distal tip portion 7. The distal tip portion 7 can include metal, such as being constructed primarily of metal. The distal tip portion 7 can include a strut attached to the outside wall of the first main lumen and extending distally and attached at a second point to the second lumen at a point distal to the termination of the first lumen, such as to provide a guard inhibiting suction of the artery or vein wall against the first lumen opening. In an embodiment, the 0.5-2.0 mm of the distal tip can be coated with gold.

Figure 4:
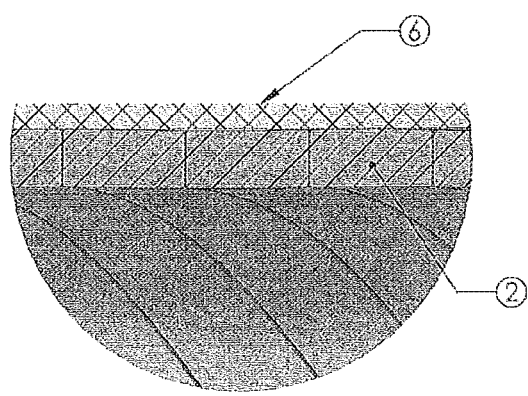
FIG. 4 is a section view of a portion of the wall of the first lumen While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

FIG. 4 shows a cross-section of a portion of the wall of the first lumen. The first lumen can include a polymeric layer 6. The first lumen can include a multi-filar coil structure 2. The internal surface of the first lumen can be coated with a silicone friction reducing polymer.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A vascular interventional catheter comprising:
   a catheter body extending between a catheter proximal end and a catheter distal end, the proximal end configured for coupling with a vacuum source, the catheter body includes:

a first lumen sidewall surrounding a first lumen, the first lumen sidewall extends between the catheter proximal and distal ends;
wherein the first lumen sidewall includes a distal multi-filar coil structure proximate the catheter distal end, the distal multi-filar coil structure includes rectangular coil wire cross sections having rectangular edges in intimate contact with adjacent rectangular edges of other rectangular coil wire cross sections;
wherein the first lumen sidewall includes a metal tube extending between the catheter proximal end to at least the distal multi-filar coil structure, the metal tube fused to the distal multi-filar coil structure;
a second lumen sidewall surrounding a second lumen, the second lumen sidewall and the second lumen are proximate the catheter distal end and remote from the catheter proximal end, the second lumen sidewall extending along the first lumen sidewall; and
a tapered distal tip coupled with the distal multi-filar coil structure proximate the catheter distal end, wherein the tapered distal tip includes a distal tip opening in communication with the first lumen.

2. The vascular interventional catheter of claim 1, wherein the second lumen sidewall terminates along the first lumen sidewall distally relative to the catheter proximal end.

3. The vascular interventional catheter of claim 1, wherein the second lumen of the second lumen sidewall is configured for reception of a guidewire rail.

4. The vascular interventional catheter of claim 1, wherein the first lumen sidewall includes a proximal opening in communication with a luer adapter.

5. The vascular interventional catheter of claim 1, wherein an angle of the distal tip opening corresponds with the taper of the tapered distal tip.

6. The vascular interventional catheter of claim 1, wherein a cross section of the catheter body includes one or more of inner or outer polymer jackets and further includes a metallic composition of between 35 and 65 percent of the cross sectional composition.

7. The vascular interventional catheter of claim 1, wherein the intimate contact between the rectangular edges includes an intimate wire matrix of filars of the distal multi-filar coil structure.

8. The vascular interventional catheter of claim 1, wherein the distal multi-filar coil structure includes one or more filars each having a polymer coating.

9. A vascular interventional catheter comprising:
a catheter body extending between a catheter proximal end and a catheter distal end, the proximal end configured for coupling with a vacuum source, the catheter body includes:
a first lumen sidewall surrounding a first lumen, the first lumen sidewall extends between the catheter proximal and distal ends;
wherein the first lumen sidewall includes a distal multi-filar coil structure proximate the catheter distal end;
the distal multi-filar coil structure includes rectangular coil wire cross sections having rectangular edges extending along adjacent rectangular edges of other rectangular coil wire cross sections;
a metal tube joined with a proximal end of the distal multi-filar coil structure, the metal tube extends from the distal multi-filar coil structure to the catheter proximal end;
a second lumen sidewall surrounding a second lumen and extending along the first lumen sidewall, the second lumen sidewall and the second lumen are proximate the catheter distal end and remote from the catheter proximal end; and
a tapered distal tip including metal, the metal of the tapered distal tip is joined with the distal multi-filar coil structure proximate the catheter distal end, and the tapered distal tip includes a distally extending taper.

10. The vascular interventional catheter of claim 9, wherein the second lumen sidewall terminates along the first lumen sidewall distally relative to the catheter proximal end.

11. The vascular interventional catheter of claim 9, wherein the first lumen of the first lumen sidewall is configured for aspirating in vasculature, and the first lumen sidewall includes a distal opening.

12. The vascular interventional catheter of claim 11, wherein the first lumen sidewall includes a proximal opening in communication with a luer adapter.

13. The vascular interventional catheter of claim 11, wherein the first lumen sidewall at the catheter distal end is angled to increase a cross-sectional size of the distal opening.

14. The vascular interventional catheter of claim 9, wherein a cross section of the catheter body includes one or more of inner or outer polymer jackets and further includes a metallic composition of between 35 and 65 percent of the cross sectional composition.

15. The vascular interventional catheter of claim 9, wherein the rectangular edges of the rectangular coil wire cross sections are in intimate contact along adjacent rectangular edges of other rectangular coil wire cross sections.

16. The vascular interventional catheter of claim 9, wherein the distal multi-filar coil structure includes one or more filars each having a polymer coating.

17. The vascular interventional catheter of claim 9, wherein the distally extending taper of the tapered distal tip is at an angle of between 30 to 60 degrees relative to a central axis of the first lumen side wall and the first lumen.

* * * * *